(12) United States Patent
Gastner et al.

(10) Patent No.: US 8,536,222 B2
(45) Date of Patent: *Sep. 17, 2013

(54) ADDITION COMPOUNDS OF GUANIDINOACETIC ACID

(75) Inventors: Thomas Gastner, Engelsberg (DE); Hans-Peter Krimmer, Kirchweidach (DE)

(73) Assignee: AlzChem AG, Trostberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/425,893

(22) Filed: Mar. 21, 2012

(65) Prior Publication Data

US 2012/0238629 A1      Sep. 20, 2012

Related U.S. Application Data

(63) Continuation-in-part of application No. 11/885,375, filed as application No. PCT/EP2006/001908 on Mar. 2, 2006, now Pat. No. 8,153,685.

(30) Foreign Application Priority Data

Mar. 4, 2005   (DE) .......................... 10 2005 009 990

(51) Int. Cl.
  *A01N 43/30*   (2006.01)
  *A01N 43/26*   (2006.01)
  *A01N 43/16*   (2006.01)

(52) U.S. Cl.
  USPC ............ 514/464; 514/440; 514/460; 514/554

(58) Field of Classification Search
  USPC .................................. 514/464, 440, 460, 554
  See application file for complete search history.

(56) References Cited

U.S. PATENT DOCUMENTS

| 5,939,078 | A * | 8/1999 | Fujimura et al. ............... 424/401 |
| 6,242,491 | B1 | 6/2001 | Kaddurah-Daouk |
| 6,855,727 | B2 | 2/2005 | Matahira et al. |
| 7,186,754 | B2 | 3/2007 | Kaddurah-Daouk |
| 2002/0049253 | A1 | 4/2002 | Kaddurah-Daouk |
| 2005/0287204 | A1 | 12/2005 | Hageman et al. |
| 2007/0231370 | A1 | 10/2007 | Gastner et al. |
| 2011/0257075 | A1 | 10/2011 | Gastner et al. |

FOREIGN PATENT DOCUMENTS

| CA | 2569269 | 12/2005 |
| GB | 1 195 199 A | 6/1970 |
| GB | 1 195 200 A | 6/1970 |
| JP | 61-231996 A | 10/1986 |
| JP | 09-202710 A | 8/1997 |
| JP | 10-017442 | 1/1998 |
| WO | WO 91/07954 A | 6/1991 |
| WO | WO 01/00203 A | 1/2001 |
| WO | WO 2004/000297 A | 12/2004 |
| WO | WO 2005/120246 A | 12/2005 |

OTHER PUBLICATIONS

De Miranda, et al. "Study on guanidino-carboxylate interaction in copper(II)ternary complexes of guanidinoacetic acid with glutamic and aspartic acids", *Polypehdron* 22 (2003) pp. 225-233.

Robyn, Y. "Biological distribution of guanidines and phosphagens in marine annelid and related phyla from California, with a note on pluriphosphagens", STN Doc. No. 62:4409 , *Compar. Biochem. Physiol.* 12(3) (1964), pp. 347-367, Abstract.

Thoai, et al. "Two new phosphagens: phosphotaurocyamime and phosphoglycocyamine", STN Doc. No. 48:33638 *Comptes Rendus des Seances de la Societe de Biologie et de Ses Fillales* (1953), 147, pp. 1241-1243 (Abstract).

* cited by examiner

*Primary Examiner* — Nizal Chandrakumar
(74) *Attorney, Agent, or Firm* — Fulbright & Jaworski LLP

(57) ABSTRACT

The present invention provides new addition compounds of guanidinoacetic acid with malic acid, aspartic acid, ascorbic acid, succinic acid, pyruvic acid, fumaric acid, gluconic acid, alpha-ketoglutaric acid, pyroglutamic acid, 3-nicotinic acid, lactic acid, citric acid, maleic acid, acetic acid, formic acid, 2-hydroxybenzoic acid, L-carnitine, acetyl-L-carnitine, taurine, betaine, choline, methionine and lipoic acid as well as in the form of sodium, potassium or calcium guanidinoacetate. These addition compounds have improved physiological and therapeutic properties and are particularly suitable for use as dietary supplements, as animal feeds and in cosmetic or dermatological preparations in which especially the marked stability and good bioavailability of the addition compounds come to the fore.

23 Claims, 7 Drawing Sheets

KETOGLUTARIC ACID

ADDITION COMPOUND GAA - KETOGLUTARIC ACID

CITRIC ACID - ANHYDRATE (FREE OF WATER)

ADDITION COMPOUNDS OF GUANIDINOACETIC ACID

Figure 1:
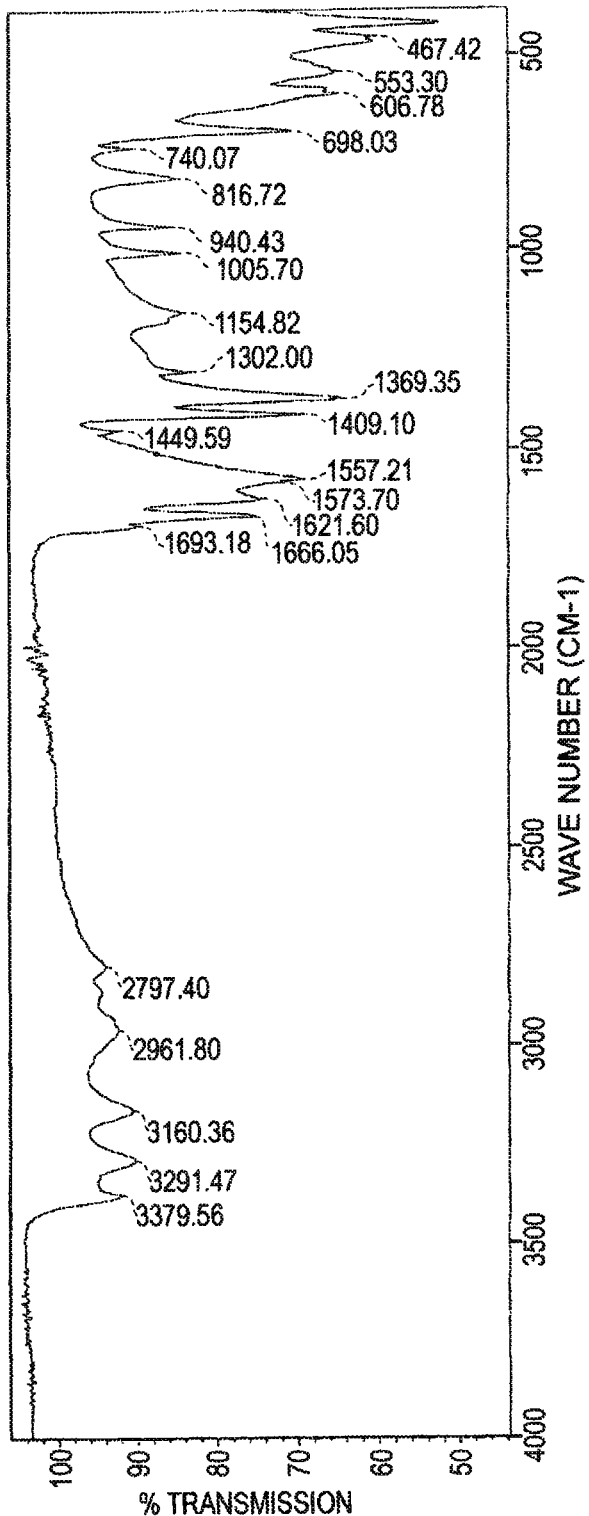
Figure 1:
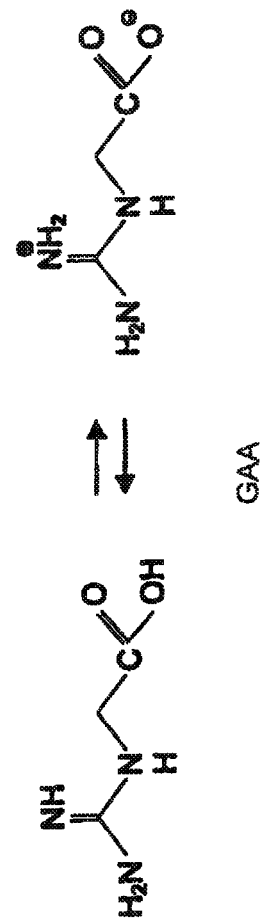

This application is a continuation-in-part application of U.S. Ser. No. 11/885,375 filed Aug. 30, 2007 now U.S. Pat. No. 8,153,685, incorporated herewith by reference in its entirety, which is a §371 of PCT/EP2006/001908 filed Mar. 2, 2006. This application also claims priority from German 10 2005 009 990.4 filed Mar. 4, 2005.

The present invention concerns the preparation of new addition compounds of guanidinoacetic acid. They have improved physiological and therapeutic properties and are suitable for use as food supplements, animal feeds and in cosmetic or dermatological preparations in which especially their marked stability and good bioavailability of the addition compounds come to the fore.

Guanidinoacetic acid (GAA) is an endogenous substance which occurs in humans and plays a central role in the biosynthesis of creatine. Creatine is of major importance for the energy metabolism of the cell and it is taken up from the food and can also be formed by the body. The biosynthesis starts from glycine and L-arginine. In mammals the guanidine group of L-arginine is cleaved and an N—C—N group is transferred to glycine by the enzyme amidinotransferase above all in the kidneys, but also in the liver and pancreas. In this process L-arginine is converted into L-ornithine. The guanidinoacetic acid formed in this manner is converted into creatine in the next step with the aid of the enzyme methyltransferase and this occurs exclusively in the liver in the case of vertebrates.

Creatine in the form of energy-rich phosphocreatine is an important energy reserve of muscle in addition to adenosine triphosphate (ATP). When the muscle is in a resting state, ATP can transfer a phosphate group to creatine to form phosphocreatine which is then in direct equilibrium with ATP. During muscular work it is of decisive importance to fill up the ATP stores again as rapidly as possible. Phosphocreatine is available for this purpose in the first seconds of maximum muscular load. The enzyme creatine kinase can transfer a phosphate group from phosphocreatine to adenosine diphosphate in a very rapid reaction and thus re-form ATP. This is also referred to as the Lohmann reaction.

In the nineties creatine monohydrate became a popular dietary supplement due to its unique function in energy metabolism. The sports industry uses creatine monohydrate to increase the pool of energy-rich phosphate compounds in the body during training and to improve the body-mass index. Recent studies with creatine yielded positive therapeutic results for diverse clinical applications [Persky, A. M.; Brazeau, G. A.: Clinical Pharmacology of the Dietary Supplement Creatine Monohydrate. In: Pharmacol. Rev. 2001, 53, 161-176]. In addition to creatine itself i.e. creatine monohydrate, numerous creatine salts such as creatine ascorbate, creatine citrate, creatine pyruvate and others have also in the meantime proven to be suitable dietary supplements or therapeutic agents. The European Patent EP 894 083 and the German laid-open Patent Application DE 197 07 694 A1 are mentioned here as representatives.

In a series of scientific papers it was shown that creatine and its salts lead to an increase in fat-free muscle mass and muscle performance. Thus it is also known that the pancreas secretes more insulin under the influence of guanidine compounds such as creatine and guanidinoacetic acid, and guanidinoacetic acid is substantially better at stimulating the secretion of insulin than creatine itself. Insulin promotes the uptake of glucose and amino acids into muscle cells and thus promotes protein synthesis. It is also advantageous that insulin catalyses the uptake of creatine into muscles. In addition insulin reduces the rate of degradation of the musculature.

Positive effects have also been found in animals and creatine monohydrate was therefore recommended for use as a feed additive and has a meat meal substitute in animal nutrition. Since the prohibition of animal proteins in feedstuffs in the year 2000 in the EU, many diets for breeding animals and fattened animals have been converted to pure vegetarian diets, and fish meal which was not covered by the ban has also been omitted to a large extent. The conversion to pure vegetarian diets led to losses in performance and, even after almost five years, the pure vegetarian diets are inferior to those containing animal proteins. One reason for this inferiority is the lack of creatine. Earlier experiments clearly showed that creatine monohydrate added to the feed can improve the performance when pure vegetarian diets are fed [Wallimann, T.; Pfirter, H. P.: Use of Creatine as a Feed Additive. EP1051914].

In addition to the undoubted positive effects creatine monohydrate also has some disadvantages. This compound has a very limited stability in aqueous solutions and creatine monohydrate only has a low bioavailability after oral ingestion. Furthermore, creatine monohydrate is a very expensive substance and the improvements in performance that were achieved in animal fattening are almost completely compensated by the costs.

Hence, guanidinoacetic acid which has an astounding stability in aqueous solution compared to creatine and is much more bioavailable, has also been used recently as a dietary supplement and animal feed. Guanidinoacetic acid is very efficiently and rapidly converted into creatine in the body. Hence, guanidinoacetic acid can be administered in substantially lower amounts than creatine while having the same effect. In one study, rats were fed diets containing about 0.36 g/kg guanidinoacetic acid by which means the creatine content in muscles increased by 39% compared to the comparison group [Stead, L. M.; Au, K. P.; Jacobs, R. L.; Brosnan, M. E.; Brosnan, J. T.: Methylation demand and homocysteine metabolism: Effects of Dietary Provision of Creatine and Guanidinoacetate. In: Am. J. Physiol. Endocrinol. Metab., 2001 November; 281(5); 1095-100]. The increase in creatine in muscle is due to a high conversion rate of the ingested guanidinoacetic acid into creatine. This also coincides with the observation that the enzyme transmethylase is found in very high concentrations in the liver.

In addition to its use as a dietary supplement or as an animal feed additive, guanidinoacetic acid is also suitable for cosmetic applications. Thus, WO 2001/000 203 A1 describes guanidinoacetic acid as an energy-supply system and antioxidant for the upper skin layers in which guanidinoacetic acid is mainly applied in the form of creams which protect the skin from unfavourable influences such as solar radiation and stress.

In addition to the advantages of guanidinoacetic acid compared to creatine, the compound, however, has the disadvantage of a very poor solubility in water (1 g in 278 ml water at 15° C.).

From the described disadvantages of the prior art with regard to guanidinoacetic acid, the object was posed for the present invention of improving the solubility of guanidinoacetic acid in water and to further increase the bioavailability while retaining the known good physiological properties of guanidinoacetic acid.

This object is achieved by providing new addition compounds of guanidinoacetic acid with malic acid, aspartic acid, ascorbic acid, succininic acid, pyruvic acid, fumaric acid, gluconic acid, alpha-ketoglutaric acid, pyroglutamic acid, 3-nicotinic acid, lactic acid, citric acid, maleic acid, acetic acid, formic acid, 2-hydroxybenzoic acid, L-carnitine, acetyl-L-carnitine, taurine, betaine, choline, methionine or lipoic acid.

Addition compounds of guanidinoacetic acid with malic acid, aspartic acid, ascorbic acid, succininic acid, fumaric acid, gluconic acid, alpha-ketoglutaric acid, pyroglutamic acid, 3-nicotinic acid, lactic acid, citric acid, maleic acid, acetic acid, formic acid, 2-hydroxybenzoic acid, L-carnitine, acetyl-L-carnitine or lipoic acid are preferred. Addition compounds of guanidinoacetic acid with malic acid, aspartic acid, ascorbic acid, succininic acid, fumaric acid, alpha-ketoglutaric acid, 3-nicotinic acid, lactic acid, citric acid, 2-hydroxybenzoic acid or lipoic acid are more preferred.

Addition compounds of guanidinoacetic acid with citric acid or with alpha-ketoglutaric acid are particularly preferred.

The molar ratio of guanidinoacetic acid to the second component selected from malic acid, aspartic acid, ascorbic acid, succininic acid, pyruvic acid, fumaric acid, gluconic acid, alpha-ketoglutaric acid, oxalic acid, pyroglutamic acid, 3-nicotinic acid, lactic acid, citric acid, maleic acid, sulfuric acid, acetic acid, formic acid, 2-hydroxybenzoic acid, L-carnitine, acetyl-L-carnitine, taurine, betaine, choline, methionine and lipoic acid is preferably from 5:1 to 1:5, more preferably from 2:1 to 1:2, in particular, from 1.2:1 to 1:1.2 and, most preferably, 1:1.

The inventors of the present application have found that, besides salts, also addition compounds of guanidinoacetic acid with other compounds can be formed. Salts are characterized by a complete proton transition of the compound to guanidinoacetic acid. In the case of salts, the guanidinoacetic acid, thus, is present unipositively charged. Salts are formed, in particular, when the $pK_a$ value of the compound is clearly lower than the $pK_a$ value of guanidinoacetic acid. GAA has a $pK_a$ value of approximately 3.3 (±0.1; calculated). The formation of salts is mostly observed also when preparing substances comprising guanidinoacetic acid and at least a second compound in a solvent, in particular, in water.

It has now been found that, besides salts, also addition compounds of guanidinoacetic acid with other compounds can be formed. Thereby, interactions take place, without complete proton transfer occurring. Such addition compounds, thus, differ from salts but also from simple physical mixtures. Addition compounds are particularly formed if the second component has a $pK_a$ value of 1.9 or more, preferably of 2.3 or more and of up to 6.5 or less, preferably 5.4 or less, more preferably 4.8 or less and, in particular, 3.5 or less. Preferably, the second component has a $pK_a$ value from 1.9 to 6.5, in particular, from 2.0 to 4.8 and, more preferred, from 2.3 to 3.5. The decisive $pK_a$ value thereby is the first $pK_a$ value.

Further, it has been found that addition compounds are formed especially when the starting materials, i.e. guanidinoacetic acid and the second compound, are dryly mixed without the addition or presence of any solvent, in particular, without the addition or presence of any water.

The $pK_a$ values of the preferred second compounds are as follows:
citric acid: 3.1; alpha-ketoglutaric acid: 2.3; aspartic acid: 2.0; 2-hydroxybenzoic acid: 2.8; fumaric acid: 3.0; malic acid: 3.4; lactic acid: 3.9; ascorbic acid: 4.2; succinic acid: 4.2; lipoic acid: 5.4; 3-nicotinic acid: 4.8.

The inventive addition compounds can be determined and distinguished, respectively, from salts or purely physical mixtures, for example, by their IR spectrum as well as by means of DSC measurements. In the IR spectrum, new bands or shifts of bands seen in the educts can be observed, with the characteristic carboxylate bands, however, being preserved.

In the DSC, addition compounds have several melting points or a broad melting range, whereas salts have a single narrow melting range.

The addition compounds of the present invention, in particular, show bands in the IR spectrum having wave numbers of the carboxylate bands of the guanidinoacetic acids, i.e. at $1573\pm10$ cm$^{-1}$, in particular, at $1573\pm5$ cm$^{-1}$ as well as at $1369\pm10$ cm$^{-1}$, in particular, at $1369\pm5$ cm$^{-1}$ as well as a band of the guanidino group at $3160\pm10$ cm$^{-1}$, in particular, at $3160\pm5$ cm$^{-1}$. Further, they show bands of the carboxylate group of the second compound. In the case of a guanidinoacetic acid—citric acid addition compound, the latter, thus, shows bands at $1743\pm10$ cm$^{-1}$, in particular, at $1743\pm5$ cm$^{-1}$ as well as at $1695\pm10$ cm$^{-1}$, in particular, at $1695\pm5$ cm$^{-1}$.

In the case of a guanidinoacetic acid—alpha-ketoglutaric acid addition compound, the latter shows bands at $1706\pm10$ cm$^{-1}$, in particular, at $1706\pm5$ cm$^{-1}$ as well as at $1693\pm10$ cm$^{-1}$, in particular, at $1693\pm5$ cm$^{-1}$.

Further, in addition compounds, compared to mere mixtures, at least some bands in the IR spectrum are shifted with respect to their wavelength or changed with respect to their intensities.

The inventive addition compounds are preferably present in a solid state, in particular, in powdery form. They particularly contain little or no solvent, in particular, $\leq 1$ wt %, more preferably $\leq 0.1$ wt % solvent and, even more preferably, are totally free of solvent. "Solvent" means both organic solvents and aqueous solvents, in particular, water.

It has surprisingly turned out that not only could the object be achieved since the claimed addition compounds have a considerably higher water solubility compared to guanidinoacetic acid, but also that the new compounds are at least equal to guanidinoacetic acid with regard to their stability and bioavailability.

In addition to the new compounds of guanidinoacetic acid the present invention also concerns a composition that is physiologically effective and which contains at least one of the described addition compounds of guanidinoacetic acid according to the present invention as an active ingredient.

The present invention also encompasses the use of this composition as an animal feed, as a dietary supplement or in the medical field and especially in the form of powders, granulates, lozenges, capsules, pellets, solutions, juices or jelly products.

In this connection it may be advisable depending on the respective concrete application case to use the addition compounds of guanidinoacetic acid in combination with other physiologically active substances in which case carbohydrates, fats, amino acids, proteins, vitamins, mineral substances, trace elements and derivatives thereof and any mixtures thereof are particularly suitable.

Thus, the present invention also concerns animal feeds, dietary supplements as well as pharmaceutical preparations which contain the addition compounds according to the invention.

A further advantage in this connection has turned out to be the fact that the addition compounds of guanidinoacetic acid can be used in a relatively broad dosage range in which the single doses as well as the daily doses are not subject to serious limitations. According to the invention the claimed use takes place in single doses of 0.001 to 1 g/kg body weight and/or in daily doses of 0.001 to 50 g.

If the use according to the invention is as a dietary supplement for humans, which takes preferential consideration, uses in the school, sport, convalescence and/or in the geriatric field come in particular into consideration.

The use of the addition compounds of guanidinoacetic acid as a feed additive is regarded as being preferred especially for animals in competitive sports. In addition the new addition compounds of guanidinoacetic acid can be used as a feed substitute for wet and dry feeds for dogs and cats in which positive effects on the immune system and the general conditions of the animals deserve special note.

Furthermore, the claimed addition compounds of guanidinoacetic acid can also be used as a feed additive for breeding animals and fattened animals and in this connection especially for pigs, horses, poultry and fish where their use as a substitute for animal and/or fish meal as well as for products produced therefrom has proven to be particularly advantageous. In this connection the substitution can be a partial or complete substitution.

The inventive guanidinoacetic acid addition compounds, in particular, can be employed in a method comprising increasing creatine in the muscle of a subject, in a method comprising increasing muscle mass of a subject as well as in a method comprising increasing the bioavailability of guanidinoacetic acid in a subject. The subject can be a mammal such as a human, dog, cat, pig or horse, or the subject can be a chicken.

The addition compounds of guanidinoacetic acid can also be used within the scope of the present invention in cosmetic or dermatological preparations in accordance with the fields of application that are known for example for creatine. This results in considerable advantages for the formulation due to the high stability and solubility of the claimed compounds, and synergistic effects with regard to efficacy between guanidinoacetic acid and the respective reaction partners are also observed. Preferred preparations are those which are present in the form of creams, lotions, sprays, mousse, aqueous or aqueous-ethanolic solutions, impregnation media for cloths, water-free or water-containing crayons or microemulsions. The topical application fields is regarded as being especially preferred.

Overall the new stable addition compounds of guanidinoacetic acid of the present invention offer much more than only new alternatives to the known creatine compounds and free guanidinoacetic acid because the properties of the new addition compounds of guanidinoacetic acid overcome the disadvantages of the known compounds above all in the preferred application fields and are thus very considerable improvements.

Figure 2:
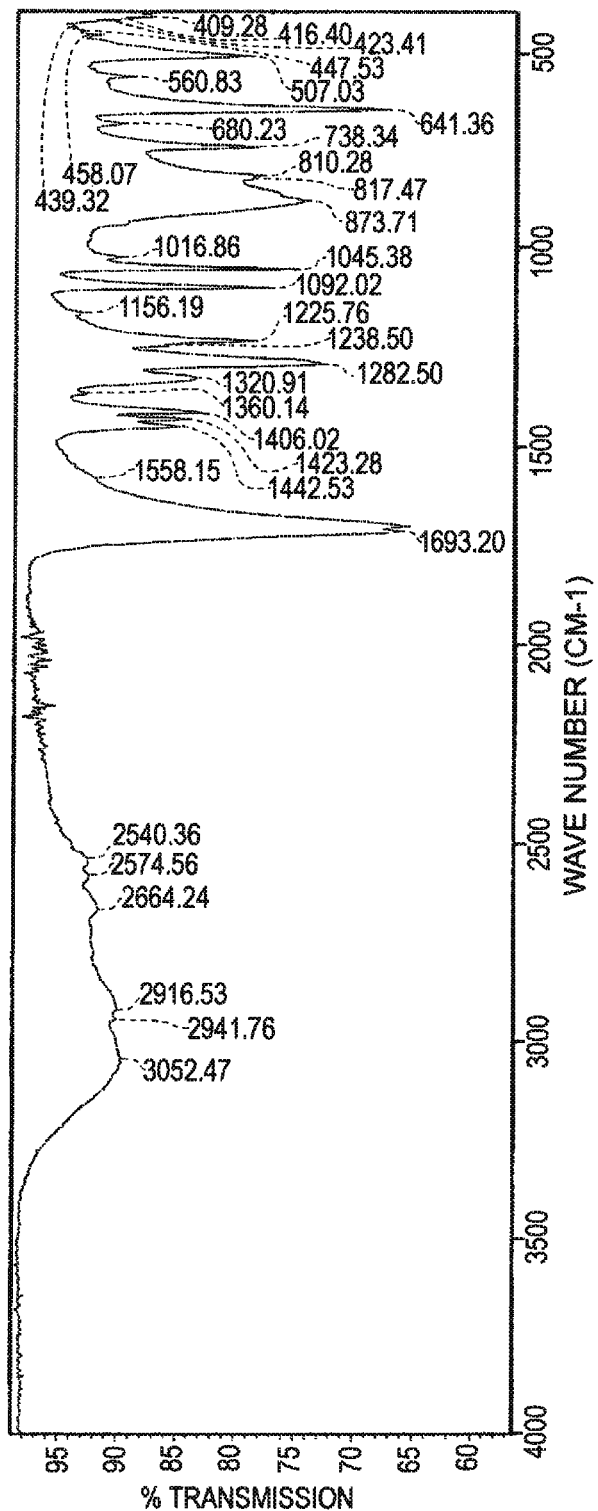
Figure 2:
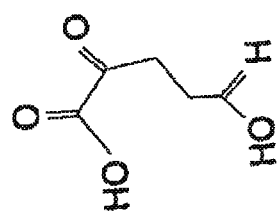
Figure 3:
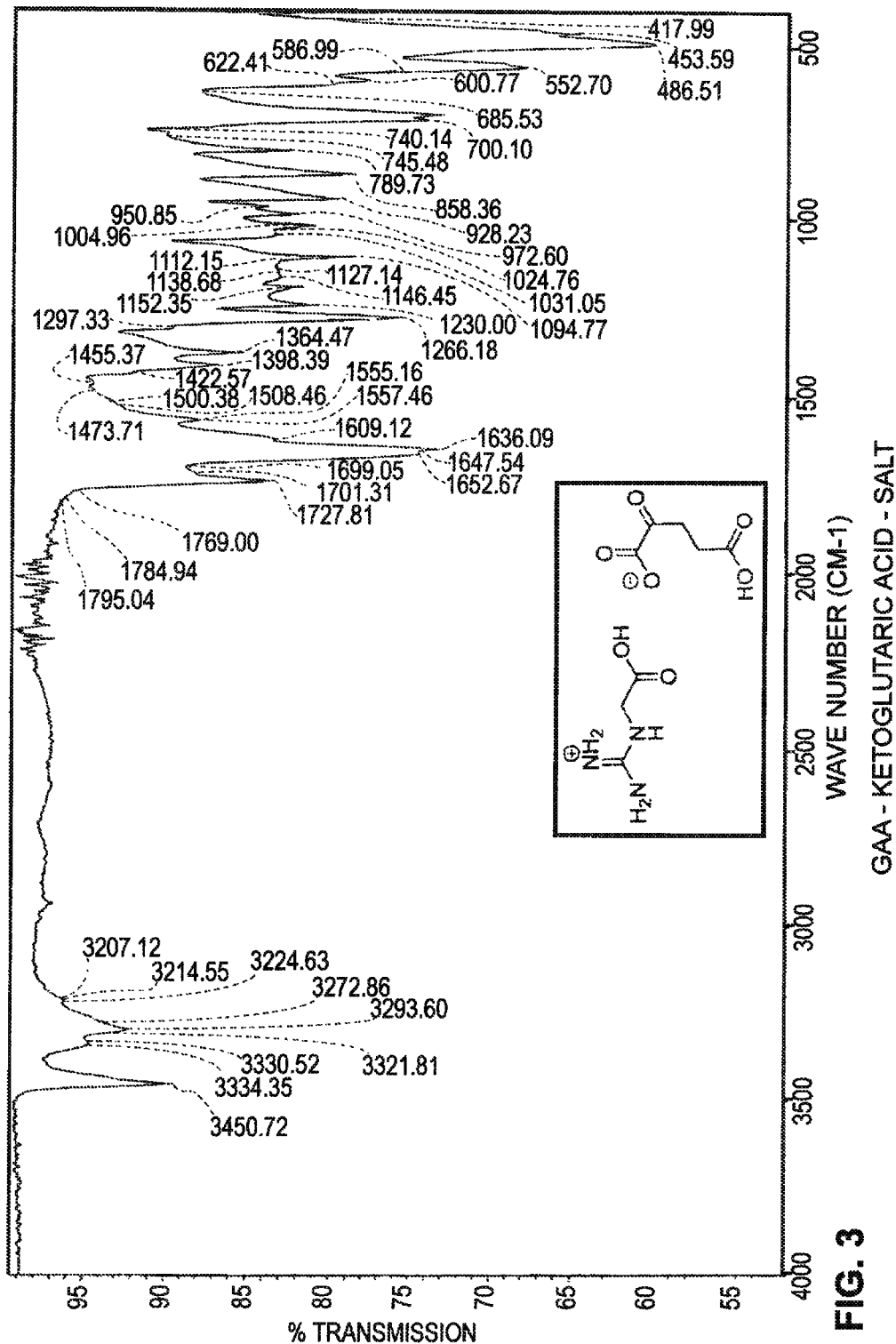
Figure 4:
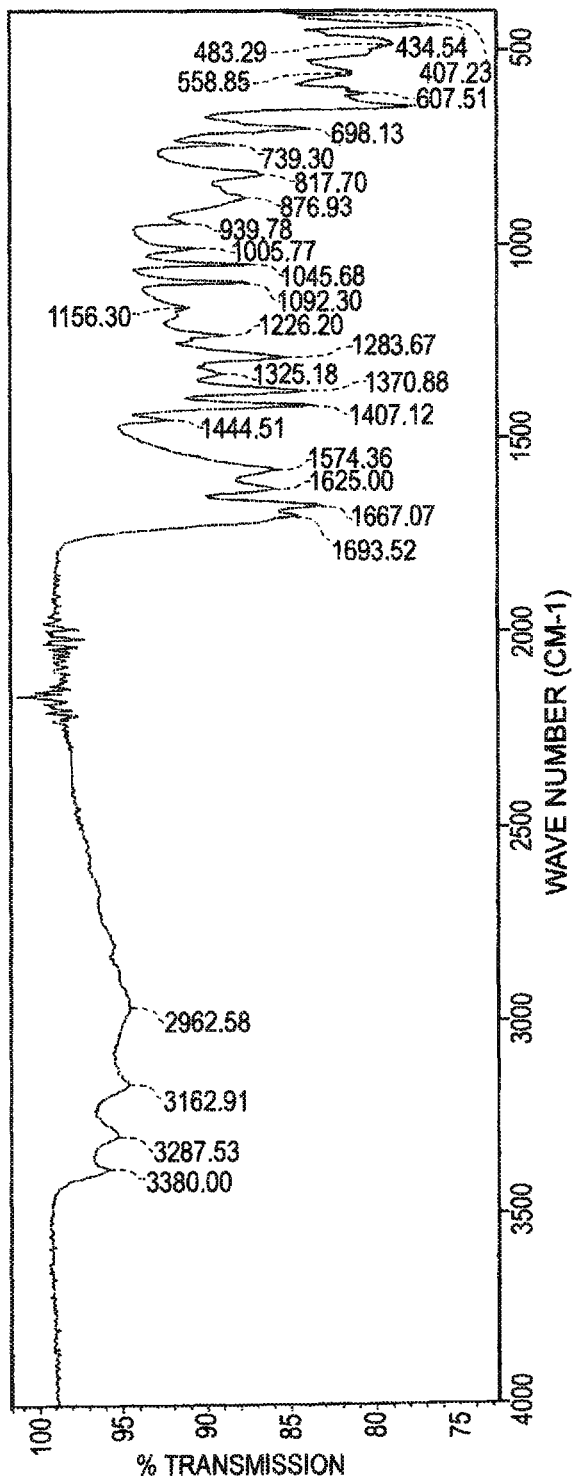
Figure 4:
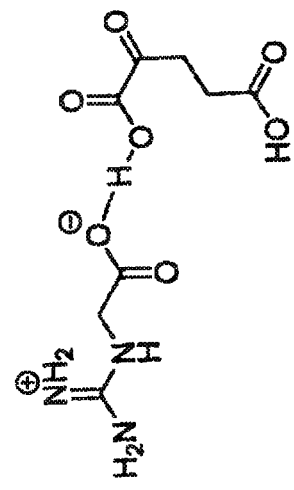
Figure 5:
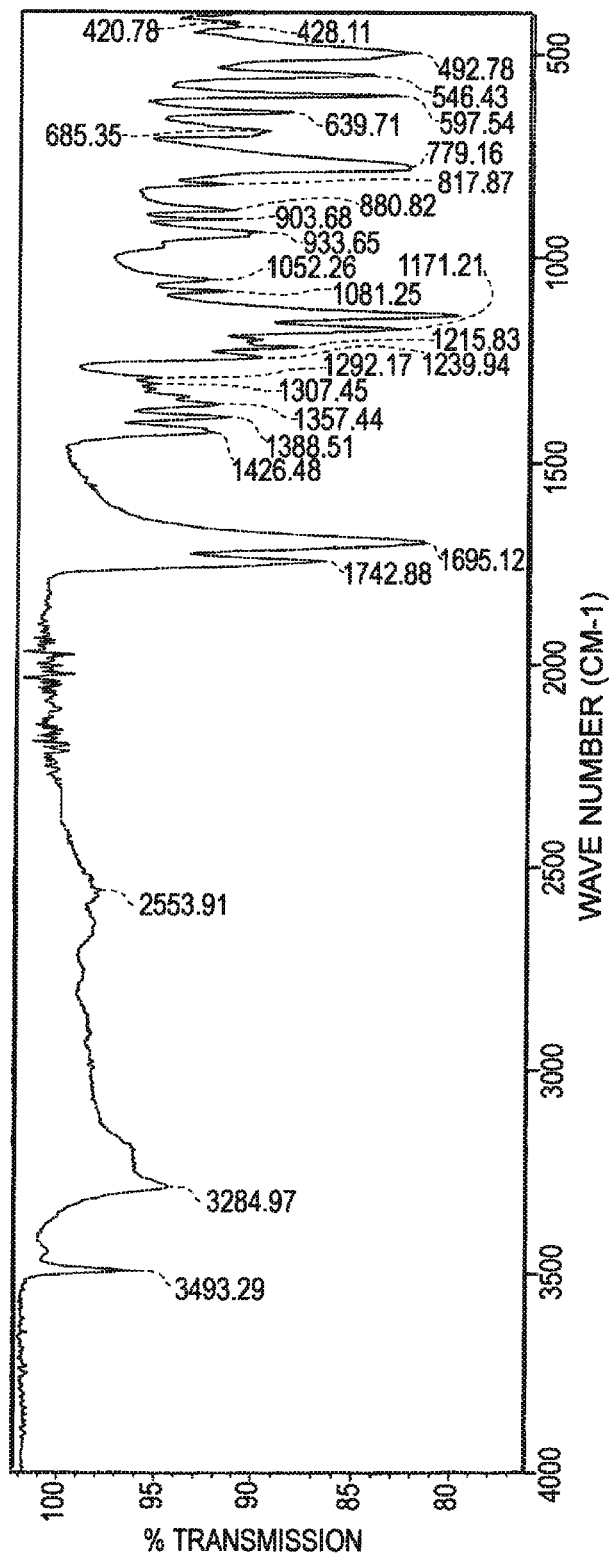
Figure 5:
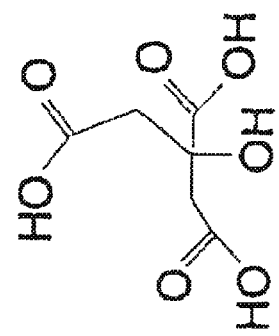
Figure 6:
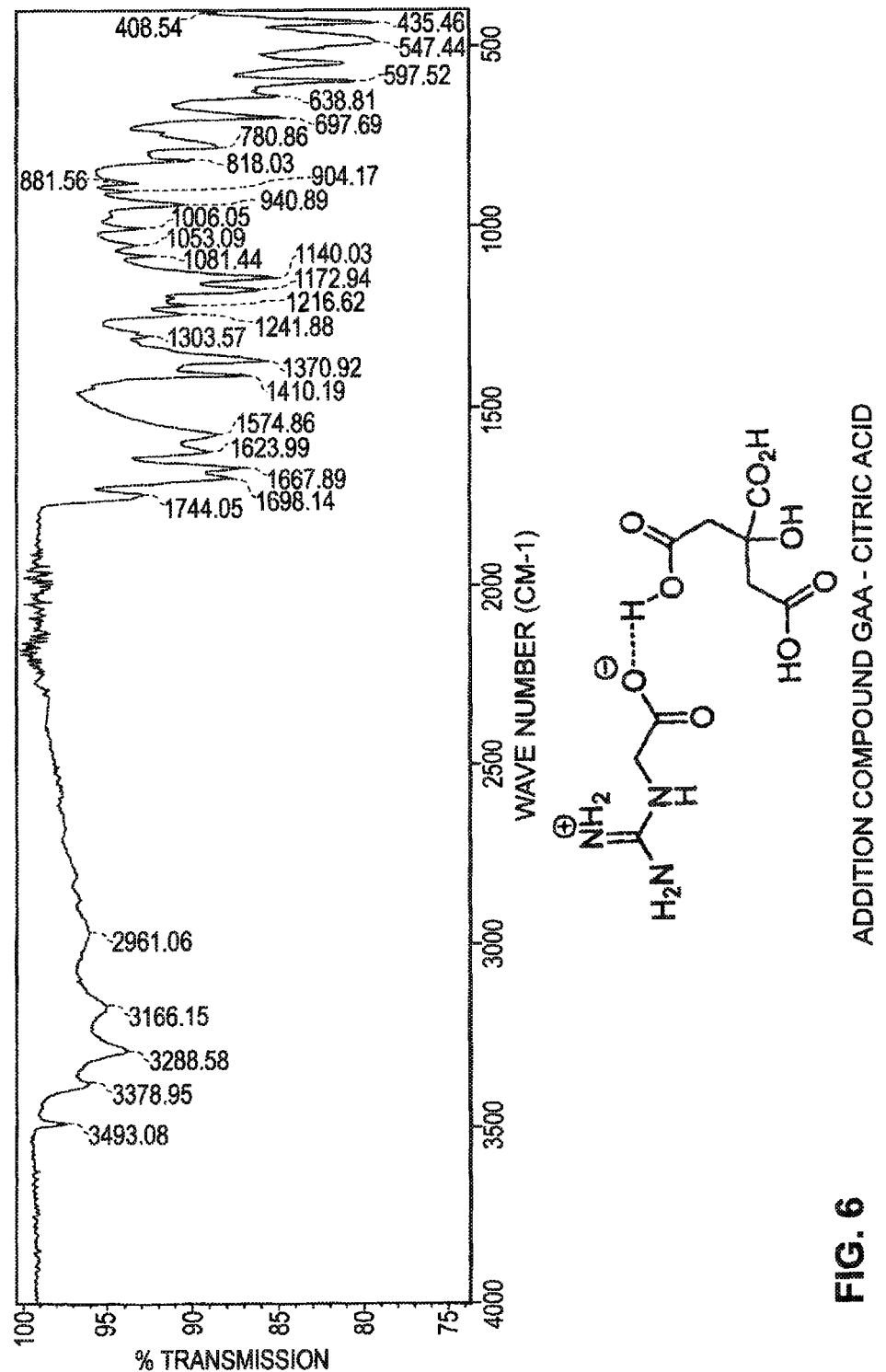
Figure 7:
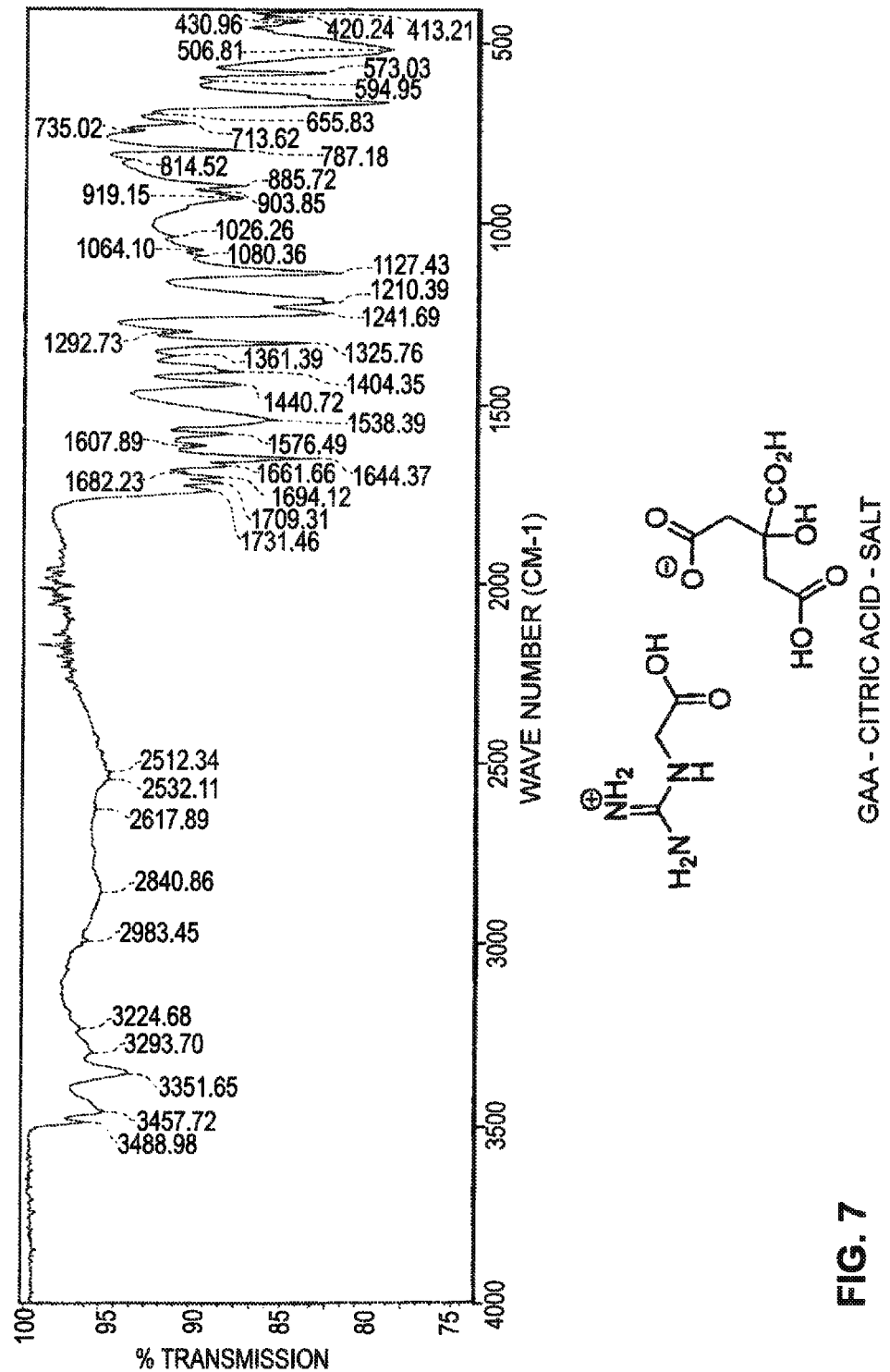

The enclosed Figures show IR spectra of
FIG. 1 guanidinoacetic acid
FIG. 2 alpha-ketoglutaric acid
FIG. 3 guanidinoacetic acid—alpha-ketoglutaric acid salt
FIG. 4 an addition compound of guanidinoacetic acid with alpha-ketoglutaric acid
FIG. 5 citric acid anhydrate
FIG. 6 an addition compound of guanidinoacetic acid with citric acid, and
FIG. 7 guanidinoacetic acid—citric acid salt.

The following examples illustrate the breadth of the present invention.

EXAMPLES

1. Dietary Supplement

Typical compositions of tasty formulations are listed in the following whose components have simply been mixed in a dry form at room temperature. It is recommended to dissolve the powder formulations in 200 ml fruit juice and/or water before their oral ingestion.

1.1 1500 mg glucosamine
 750 mg guanidinoacetic acid alpha-ketoglutarate
 720 mg magnesium L-hydrogen aspartate
 2000 mg glucose
 500 mg ascorbic acid
1.2 400 mg chondroitin sulfate
 500 mg guanidinoacetic acid pyruvate
 2000 mg dicalcium phosphate
 400 mg $(MgCO_3)_4.Mg(OH)_2.H_2O$=about 100 mg
 500 mg vitamin C
1.3 1.000 mg glucosamine
 300 mg chondroitin sulfate
 2800 mg guanidinoacetic acid aspartate
 3100 mg creatinol-O-phosphate

2. Feed Additive 2.1 A formulation consisting of 5000 mg guanidinoacetic acid malate and 5000 mg inulin was introduced into a typical formulation of feed pellets as a feed supplement for horses.
2.2 A formulation consisting of 7000 mg guanidinoacetic acid lactate, 750 mg carnitine tartrate, 100 mg sucrose stearate, 160 mg talcum and 1090 mg fructose was introduced into the basic bulk for dog biscuits.
2.3 The following formulation was introduced homogenously as a master batch into a commercially canned cat food mixture: 3000 mg guanidinoacetic acid citrate, 3000 mg creatine, 40 mg magnesium stearate, 25 mg carboxymethyl-cellulose and 135 g lactose.
2.4 Feed for fattened chicken
 It was found that the addition of 0.2% by weight guanidinoacetic acid lipoate (0.2 g/kg) to the air-dried feed for a 42 day fattening period increased the end weight by 5% compared to previous feeding methods without guanidinoacetic acid. This increase in weight was achieved solely by a meat increase but not by increases in fat or water retention (improvement of the lean body mass index) whereby the meat also had an improved quality. In addition the consumption of feed decreased by about 6% compared to previous feeding methods.

3. Preparations for Cosmetic Creams 1.2% guanidinoacetic acid citrate was homogeneously introduced into a commercial water-in-oil base cream. The cream is suitable for among others treating sensitive, deficient and hypoactive skin conditions. In addition it acts against premature skin ageing and environmentally induced negative changes in the skin.

4. Structures and Interactions, Respectively, of the Functional Groups of GAA with Organic Acids 4.1 Theoretical Background
 The structures in the solid matter of organic compounds having functional groups result from the fact that acid groups of the individual molecules can interact via hydrogen bonds. The intermolecular interactions of GAA (guanidinoacetic acid) and pyruvic acid are qualitatively depicted herein for comparison. The dashed lines thereby represent the hydrogen bonds and are to be discriminated from genuine chemical bonds. Accordingly, the groups playing a decisive role are the acid groups and carboxylate groups, respectively, of GAA and of the respective reaction partner as well as the guanidine group of GAA. The structure of GAA suggests that a kind of polymeric network of GAA units can form. This is certainly also the reason why GAA dissolves only very poorly in water at 20° C.

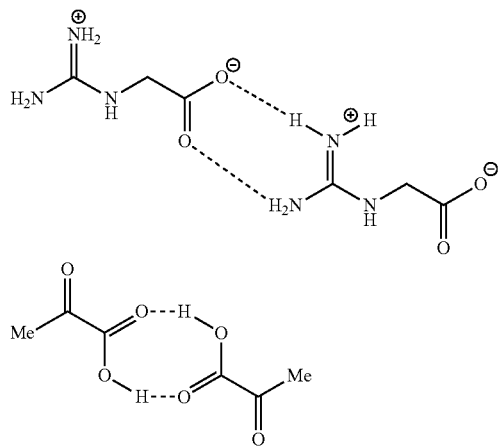

It is also possible that two different molecules (acids) interact. Thereby, a distinction must be made between salts and addition compounds. The formation of salts is due to real proton transitions, whereby this presupposes a sufficiently low $pK_a$ value (measure of the strength of an acid) of the acid. GAA has a $pK_a$ value of approximately 3.3 (±0.1; calculated). Thus, for effective formation of a salt, the employed acid must have a $pK_a$ value of clearly below 3 (note: An acid is the more acidic, the lower the $pK_a$ value is). In the example shown below using nitric acid ($pK_a=-1.3$), said salt formation is completed very rapidly due to the great difference of the $pK_a$ values and is to be regarded as quantitative.

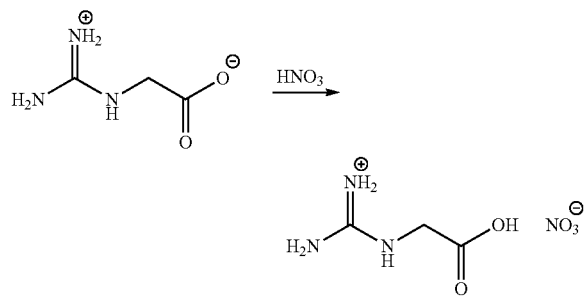

If the networks or intermolecular interactions, respectively, between one type of molecules are disrupted by adding a suitable reaction partner, the chemical environment and, thus, also the molecular and vibration characteristics change. Accordingly, significant changes in the IR spectra of the groups involved in the intermolecular interactions are clear signs of new compounds having formed, be it salts or addition compounds. However, it is possible to recognize the formation of new salty compounds in the case of well-resolved and identifiable IR spectra. The vibrations of uncharged acid groups differ significantly from those of carboxylate ions, i.e. should an acid be capable of protonating the carboxylate (=negatively charged organic acid group) of GAA, the vibrations of the carboxylate group mentioned in the following Table 1 will transform into new vibration bands. The difficulty, however, is to identify the respective relevant band in the case of overlapping vibrations and to distinguish analytical variations (variations of approximately ±2 wave numbers may occur) from true shifts. In practice, however, it is also frequently observed that the reaction of 2 reaction partners leads to hitherto undetected bands also in the solid state. The occurrence of said new bands also indicates that the two substances interact.

Another possibility of determining whether salts or addition compounds are concerned is by means of DSC analyses (Differential Scanning calorimetry). Salts should have a defined (narrow) melting range (similar to a pure substance); addition compounds, like purely physical mixtures, however, tend to have several separate melting ranges or a large undefined melting range. Said melting ranges need not correspond with those of the pure substance because a decrease of the melting point due to the addition of foreign substances is a widely found phenomenon in organic chemistry.

Thus, basically the following criteria can be drawn up for the presence of an addition compound:

1. no defined narrow melting range visible in the DSC spectrum
2. minor but significant changes of the bands involved in structure determination
3. carboxylate group of the GAA must be still discernible 4.2 Experimental Setup The following devices were used for determining the properties:

IR: Nexus FT—IR having an ATR measurement cell

DSC: Metler Toledo with Intracooler DSC 822$^e$

Measurement accuracy: ±2 cm$^{-1}$

When using IR spectroscopy, specifically the following wave numbers were determined for the individual compounds tested, namely guanidinoacetic acid, citric acid and alpha-ketoglutaric acid:

TABLE 1

Hitherto determined characteristic wave numbers.

| Wave Number (Intensity) | GAA |
|---|---|
| 3380 (m) | H-bridges, N—H-band |
| 3291 (m) | H-bridges, N—H-band |
| 3160 (m) | H-bridges, N—H-band |
| 2961 (w) | H-bridges, N—H-band |
| 2797 (w) | H-bridges, N—H-band |
| 1693 (w) | Guanidino band |
| 1666 (s) | Guanidino band |
| 1622 (m) | Guanidino band |
| 1573 (m) | Carboxylate band |
| 1369 (s) | Carboxylate band |

| Wave Number (Intensify) | Citric Acid |
|---|---|
| 3493 (m) | OH-band OH-group |
| 3285 (m) | H-bridge |
| 1743 (s) | C═O-band |
| 1695 (vs) | C═O-band |
| 1171 (s) | C—O-band |
| 1137 (vs) | C—O-band |

TABLE 1-continued

Hitherto determined characteristic wave numbers.

| Wave Number | Alpha-ketoglutaric acid |
|---|---|
| 3050 (br) | H-bridge |
| 1706 (vs) | C=O-band |
| 1693 (vs) | C=O-band |
| 1282 (s) | OH-vibration |
| 1092 (s) | C—O-band 1 |
| 1045 (s) | C—O-band 2 |

Note:
The intensities of the band are abbreviated as follows: (w) = weak; (m) = medium; (s) = strong; (vs) = very strong; (br) = broad;

4.3 Addition Compounds of GAA

The individual GAA combinations were each prepared, on the one hand, dryly without any solvent and, on the other hand, using water as solvent, followed by drying of the substance.

4.3.1 GAA: Citric Acid

There are several possibilities as to how a potential addition compound might exactly look like. Moreover, one or two carboxyl groups of citric acid may interact with GAA, resulting in a molar ratio of GAA to citric acid in the addition compound of from 1:1 to 1:2. Moreover, citric acid has a different $pK_a$ value for each of the 3 acid groups: 3.13; 4.76 and 6.4. Since the $pK_a$ of GAA is 3.3, one acid group of citric acid can be capable of creating a salt compound with GAA.

4.3.1.1 Dryly Prepared GAA:Citric Acid

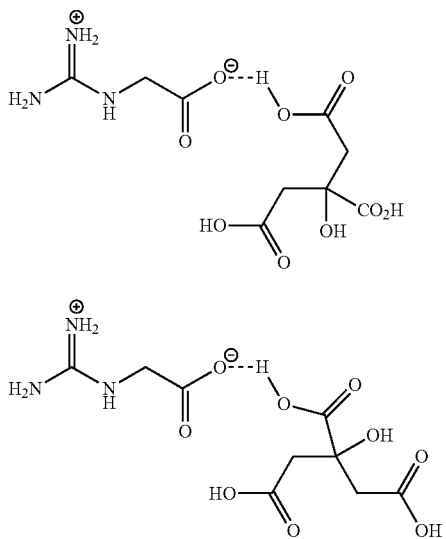

In the IR spectrum of the dryly prepared substance of GAA:citric acid, no significant shifts of the vibrations compared to those of the single compounds as listed in Table 1 can be observed. Salt formation cannot be demonstrated in the case of said compound because the carboxylate bands of GAA could be detected almost unchanged as well. While for some vibrations indeed major shift could be seen, this does not apply to most of the vibrations. However, since the two strong C=O vibrations of citric acid clearly lost intensity, one can definitely speak of a change of the environment of citric acid and, thus, of an interaction of the two molecules.

DSC analysis also confirms that no salt having a defined melting range has formed because two melting ranges can be seen.

Thus, an addition compound of GAA with citric acid is present. Since the difference in the $pK_a$ values of GAA and citric acid is not particularly distinct, it is possible that an addition compound has formed not completely or mainly on the crystal surfaces.

TABLE 2

Wave numbers of dryly prepared „GAA citrate".

| Wave Number (Intensity) | Original Compound | Original Wave Number and Intensity | Change compared to starting material |
|---|---|---|---|
| 3493 (w) | Citric acid | 3493 (m) | 0 |
| 3379 (w) | GAA | 3380 (m) | −1 |
| 3289 (m) | GAA | 3291 (m) | −2 |
| 3166 (w) | GAA | 3160 (m) | +6 |
| 2961 (w) | GAA | 2961 (w) | 0 |
| 1744 (m) | Citric acid | 1743 (s) | −1 |
| 1698 (m) | Citric acid | 1695 (vs) | +3 |
| 1669 (s) | GAA | 1666 (s) | +3 |
| 1624 (m) | GAA | 1622 (m) | +2 |
| 1574 (m) | GAA | 1573 (m) | +1 |
| 1371 (s) | GAA | 1369 (s) | +2 |

4.3.1.2 GAA:Citric Acid Prepared in Water

The picture is totally different if "GAA citrate" is prepared in water. There are partly massive shifts of the individual bands in the IR spectrum (cf. Table 3). Therefore, the networks of GAA have disrupted, and a new compound has formed.

Thus, in the presence of water as a solvent, formation of a salty GAA citrate takes place. Water enables proton transition from citric acid to GAA. Due to the small difference in the $pK_a$ values the time factor should play a role as well, as is shown by the carboxylate bands which are still weakly present. Bands could be recognized which might indicate the presence of the zwitterionic GAA (cf. the last two bands of Table 3). However, said bands have clearly lost intensity compared to the pure substance. The origin of the bands at 1709 and 1644 could not yet be clarified either; it might be an indication of the presence of a further species. The DSC spectrum of said compound has only one defined melting range.

TABLE 3

Wave numbers of wet chemically prepared „GAA citrate".

| Wave Number (Intensity) | Original Compound | Original Wave Number and Intensity | Change compared to starting material |
|---|---|---|---|
| 3489 (w) | Citric acid | 3493 (m) | −4 |
| 3352 (m) | GAA | 3380 (m) | −28 |
| 3294 (w) | GAA | 3291 (m) | −3 |
| 3225 (w) | GAA | 3160 (w) | +65 |
| 2984 (w) | GAA | 2961 (w) | +23 |
| 2848 (w) | GAA | 2797 (w) | +51 |
| 1731 (m) | Citric acid | 1743 (s) | −12 |
| 1709 (m) | | | |
| 1694 (m) | Citric acid | 1695 (vs) | −1 |
| 1662 (s) | GAA | 1666 (s) | −4 |
| 1644 (s) | | | |
| 1608 (m) | GAA | 1622 (m) | −14 |
| 1576 (w) | GAA | 1573 (m) | +3 |
| 1360 (w) | GAA | 1369 (s) | −9 |

In view of the available data, the following structure seems to be the most likely one for GAA:citric acid prepared in water:

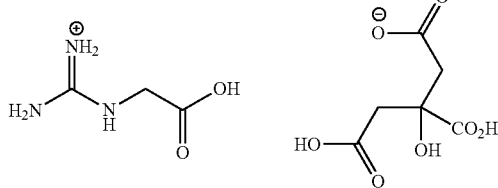

4.3.2 GAA:Alpha-Ketoglutaric Acid
4.3.2.1 Dryly Prepared GAA:Alpha-Ketoglutaric Acid A GAA:alpha-ketoglutaric acid addition compound was prepared by dryly mixing GAA with alpha-ketoglutaric acid in the absence of a solvent, in particular, in the absence of water. As can be gathered from Table 4, the bands of the starting compounds regarded as significant are detected in the IR spectrum of the end product, partly with slight shifts of the wave numbers. The characteristic double band of alpha-ketoglutaric acid at 1706 and 1693, however, has shrunken into one band. While a slight "shoulder" can be seen at this signal, no definite evaluation via the wave number can be made. Such a marked change can have happened only by a change of the chemical environment. The intensities of the bands of alpha-ketoglutaric acid shown in Table 1 cannot be reached again as far as their absolute values are concerned, however, the ratios of the bands to each other are certainly comparable (except C=O double band). The two carboxylate bands of GAA can be detected with almost unchanged intensity, with merely slight deviations.

The DSC spectrum moreover indicates 2 melting ranges which, compared to the pure substances, are each in clearly lower temperature ranges. Thus, the compound formed can be called an addition compound, since not the properties but only the chemical environment of the involved functional groups has been modified.

Unfortunately, there is only a calculated $pK_a$ value for alpha-ketoglutaric acid which, moreover, shows a very large range (2.38±0.54). Theoretically, this value is within the range of pyruvic acid, however, clear salt formation cannot be demonstrated. Thus, an addition compound comparable to the addition compound "GAA citrate" has formed.

In this context, it is possible that two structures form. Moreover, one or two carboxyl groups of alpha-ketoglutaric acid may interact with GAA.

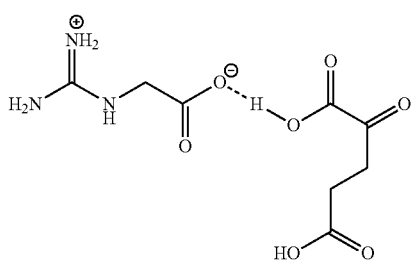

A

B

TABLE 4

Wave numbers of dryly prepared „GAA-alpha-ketoglutarate".

| Wave Number (Intensity) | Original Compound | Original Wave Number and Intensity | Change compared to starting material |
|---|---|---|---|
| 3380 (w) | GAA | 3380 (m) | 0 |
| 3288 (w) | GAA | 3291 (m) | −3 |
| 3163 (w) | GAA | 3160 (m) | +3 |
| 2963 (w) | GAA | 2961 (w) | +2 |
| 1700 (shoulder) | Ketoglutaric acid | 1706 (vs) | −6 |
| 1694 (s) | Ketoglutaric acid | 1693 (vs) | +1 |
| 1667 (s) | GAA | 1666 (s) | +1 |
| 1625 (m) | GAA | 1622 (m) | +3 |
| 1577 (m) | GAA | 1573 (m) | +4 |
| 1371 (m) | GAA | 1369 (s) | +2 |
| 1284 (m) | Ketoglutaric acid | 1282 (s) | +2 |
| 1092 (m) | Ketoglutaric acid | 1092 (s) | 0 |
| 1046 (m) | Ketoglutaric acid | 1045 (s) | +1 |

4.3.2.2 Wet Chemically Prepared GAA:Alpha-Ketoglutaric Acid

The picture is different for the wet chemically prepared "GAA-alpha-ketoglutarate". As can be gathered from Table 5 in the IR spectrum, some bands newly occur in the characteristic range, which cannot be clearly attributed to any of the two starting substances. The occurrence of new bands, on the one hand, complicates assignment, however, at the same time indicates that a new compound has originated. The attributable bands partly show considerable differences in the wave numbers compared to the educts. The carboxylate bands, too, can be found only with difficulties. Since, moreover, the DSC spectrum of said compound only has one exactly defined melting range, said reaction has produced a salt rather than an addition compound.

TABLE 5

Wave numbers of wet chemically prepared „GAA-alpha-ketoglutarate".

| Wave Number (Intensity) | Original Compound | Original Wave Number and intensity | Change compared to starting material |
|---|---|---|---|
| 3451 (m) | | | |
| 3336 (w) | GAA | 3380 (m) | −44 |
| 3293 (w) | GAA | 3291 (m) | +2 |
| 2932 (w) | GAA | 2961 (w) | −29 |
| 1728 (m) | Ketoglutaric acid | 1706 (vs) | +22 |
| 1701 (w) | Ketoglutaric acid | 1693 (vs) | +8 |
| 1653 (m) | GAA | 1666 (s) | −13 |
| 1648 (m) | | | |
| 1636 (m) | GAA | 1622 (m) | +14 |
| 1609 (m) | | | |
| 1557 (m) | GAA | 1573 (m) | −16 |
| 1398 (m) | | | |

TABLE 5-continued

Wave numbers of wet chemically prepared „GAA-alpha-ketoglutarate".

| Wave Number (Intensity) | Original Compound | Original Wave Number and intensity | Change compared to starting material |
|---|---|---|---|
| 1364 (m) | GAA | 1369 (s) | −5 |
| 1266 (s) | Ketoglutaric acid | 1282 (s) | −16 |
| 1095 (m) | Ketoglutaric acid | 1092 (s) | +3 |
| 1031 (w) | Ketoglutaric acid | 1045 (s) | −14 |

In view of the available data, the following structure seems to be the most likely one:

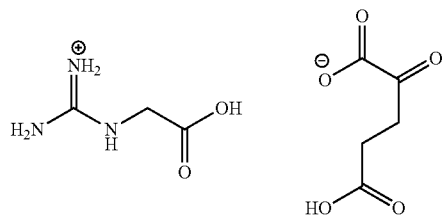 [SMILES: NC(=[NH2+])NCC(=O)O ; O=C(O)CCC(=O)C(=O)[O-]]

4.4 DSC Spectra

DSC spectra were measured from 30-300° C. at a heating rate of 10° C./min (synchronization on, dt=1.00 s)
Device: Metler Toledo with Intracooler DSC 822$^e$

TABLE 6

Survey of the melting points (═ „peak") or melting ranges, respectively, determined via DSC

| Compound | Melting Range [° C.] | Peak (maximum enthalpy change [° C.] |
|---|---|---|
| GAA | 284.5-295 | 289.5 |
| Citric acid anhydrate | 155.9-250 | 156.9 |
|  |  | 203.9 |
| Alpha-Ketoglutaric acid | 110-122 | 116.8 |
| GAA/citric acid | 104-188 (94%) | 166.8 |
| Addition compound | 245-290 (6%) | 278.4 |
| GAA/citric acid | 130-140 (1%) | 170.3 |
| Salt$^a$ | 150-210 (99%) |  |
|  | (163-195) |  |
| GAA/Alpha-Ketoglutaric acid | 82-125 (39%) | 96.8 |
| Addition compound | 134-186 (61%) | 144.4 |
| GAA/Alpha-Ketoglutaric acid Salt$^a$ | 140-180 (145-168) | 154.8 |

Note:
$^a)$In the case of the salty compounds, the total enthalpy change was counted as melting range. Actually, a closer temperature range can be seen in the spectra where melting mainly takes place. The latter is given in brackets.

4.5 Manufacturing Instruction

General manufacturing instruction for preparing the addition compounds (laboratory method):

GAA and citric acid (or alpha-ketoglutaric acid) are placed in a mortar at a molar ratio of 1:1 and mixed well with grinding (approx. 30 min). If necessary, the resulting solid is dried in vacuum at 50° C. (e.g. in the case of high humidity in the laboratory, the solid can visibly take up water from the surrounding atmosphere, agglomeration). The solid is kept tightly closed.

The invention claimed is:

1. A method comprising increasing creatine in the muscle of a subject by administering to said subject a composition comprising at least one guanidinoacetic acid addition compound comprising (i) guanidinoacetic acid and (ii) malic acid, aspartic acid, ascorbic acid, succinic acid, pyruvic acid, fumaric acid, glut acid, alpha-ketoglutaric acid, pyroglutamic acid, 3-nicotinic acid, citric acid, maleic acid, acetic acid, formic acid, 2-hydroxybenzoic acid, L-carnitine, acetyl-L-carnitine, taurine, betaine, choline or lipoic acid.

2. The method of claim 1, wherein the at least one guanidinoacetic acid addition compound comprises guanidinoacetic acid and citric acid.

3. The method of claim 1, wherein the at least one guanidinoacetic acid addition compound comprises guanidinoacetic acid and alpha-ketoglutaric acid.

4. The method of claim 1, wherein said composition further comprises at least one additional compound selected from the group consisting of carbohydrates, fats, amino acids, proteins, vitamins, mineral substances, trace elements, derivatives thereof and mixtures thereof.

5. The method of claim 1, wherein said composition is in the foitu of a powder, a granulate, a lozenge, a capsule, a pellet, a solution, a fruit juice or a jelly product.

6. The method of claim 1, wherein a sufficient amount of said composition is administered in an amount sufficient to provide a single dose of 0.001 to 1 g/kg of at least one guanidinoacetic acid addition compound per body weight of said subject.

7. The method of claim 1, wherein a sufficient amount of said composition is administered to the subject to provide a daily dose of 0.001 to 50 g of said at least one guanidinoacetic acid addition compound.

8. The method of claim 1, wherein said subject is a mammal.

9. The method of claim 2, wherein said mammal is a human, dog, cat, pig, or horse.

10. The method of claim 1, wherein the subject is a chicken.

11. The method of claim 1, wherein said subject is a human that attends school, plays sports, is a convalescent, or is a geriatric.

12. A method comprising increasing muscle mass of a subject by administering to said subject a composition comprising at least one guanidinoacetic acid addition compound comprising (i) guanidinoacetic acid and (ii) malic acid, aspartic acid, ascorbic acid, succinic acid, pyruvic acid, fumaric acid, gluconic acid, alpha-ketoglutaric acid, pyroglutamic acid, 3-nicotinic acid, citric acid, maleic acid, acetic acid, formic acid, 2-hydroxybenzoic acid, L-carnitine, acetyl-L-carnitine, taurine, betaine, choline or lipoic acid.

13. A method comprising increasing the bioavailability of guanidinoacetic acid in a subject by administering to said subject a composition comprising at least one guanidinoacetic acid addition compound comprising (i) guanidinoacetic acid and (ii) malic acid, aspartic acid, ascorbic acid, succinic acid, pyruvic acid, fumaric acid, gluconic acid, alpha-ketoglutaric acid, pyroglutamic acid, 3-nicotinic acid, citric acid, maleic acid, acetic acid, formic acid, 2-hydroxybenzoic acid, L-carnitine, acetyl-L-carnitine, taurine, betaine, choline or lipoic acid.

14. An animal feed or dietary supplement comprising at least one guanidinoacetic acid addition compound comprising (i) guanidinoacetic acid and (ii) at least one compound selected from the group consisting of malic acid, aspartic acid, ascorbic acid, succinic acid, pyruvic acid, fumaric acid, gluconic acid, alpha-ketoglutaric acid, pyroglutamic acid, 3-nicotinic acid, lactic acid, citric acid, maleic acid, acetic acid, formic acid, 2-hydroxybenzoic acid, L-carnitine, acetyl-L-carnitine, taurine, betaine, choline, methionine and lipoic acid.

15. The animal feed or dietary supplement of claim 14, wherein compound (ii) is selected from citric acid or alpha-ketoglutaric acid.

16. The method of claim 12, wherein the animal feed or dietary supplement further comprises at least one additional substance selected from the group consisting of carbohydrates, fats, amino acids, proteins, vitamins, mineral substances, trace elements, derivatives thereof and mixtures thereof.

17. The method of claim 12, wherein said animal feed or dietary supplement is in the form of a powder, a granulate, a lozenge, a capsule, a pellet, a solution, a fruit juice or a jelly product.

18. The method of claim 12, wherein a sufficient amount of said composition is administered in an amount sufficient to provide a single dose of 0.001 to 1 g/kg of said at least one guanidinoacetic acid salt per body weight of said subject.

19. The method of claim 12, wherein a sufficient amount of said composition is administered to the subject to provide a daily dose of 0.001 to 50 g of said at least one guanidinoacetic acid salt.

20. The method of claim 12, wherein said subject is a mammal.

21. The method of claim 20, wherein said mammal is a human, dog, cat, pig, or horse.

22. The method of claim 12, wherein said animal is a chicken.

23. The method of claim 12, wherein said subject is a human that attends school, plays sports, is a convalescent, or is a geriatric.

* * * * *